United States Patent
Berliner et al.

(12) 
(10) Patent No.: US 6,544,971 B1
(45) Date of Patent: Apr. 8, 2003

(54) METHOD OF INCREASING ALERTNESS BY ADMINISTRATION OF A VOMEROPHERIN, AND VOMEROPHERIN-EMITTING ALARM DEVICES

(75) Inventors: David L. Berliner, Atherton, CA (US); Louis Monti, Salt Lake City, UT (US); Clive L. Jennings-White, Salt Lake City, UT (US)

(73) Assignee: Pherin Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/498,830

(22) Filed: Feb. 4, 2000

(51) Int. Cl.[7] ............................. A61K 31/56; G08B 7/00
(52) U.S. Cl. ....................... 514/178; 514/177; 552/625; 604/19; 604/23; 604/24; 304/691.1
(58) Field of Search .................. 514/177, 178; 340/628, 577, 691.1; 552/625; 604/19, 23, 24

(56) References Cited

FOREIGN PATENT DOCUMENTS

| WO | 94 28903 | 12/1994 |
| WO | WO 94/28903 A1 * | 12/1994 |
| WO | 94 28904 | 12/1994 |

OTHER PUBLICATIONS

L. Monti Bloch, et al., "The Human Vomeronasal System", *Annals of the New York Academy of Sciences*, New York, NY, vol. 855, 1998. pp. 373–389.

L. Monti Bloch, et al., "Effect of Putative Pheromones on the Electrical Activity of the Human Vomeronasal Organ and Olfactory Epithelium", *Journal of Steroid Biochemistry and Molecular Biology*, GB, vol. 39, No. 4B, Oct. 1991, pp. 573–582,.

* cited by examiner

*Primary Examiner*—Dwayne C. Jones
(74) *Attorney, Agent, or Firm*—Heller Ehrman White & McAuliffe LLP

(57) ABSTRACT

A method of increasing alertness in an individual by administering an effective amount of an alertness-increasing vomeropherin to the individual; and an alarm device that, when activated, emits an alertness-increasing vomeropherin. The method and device are especially useful in increasing alertness in individuals who are not readily responsive to usual external stimuli.

16 Claims, No Drawings

METHOD OF INCREASING ALERTNESS BY ADMINISTRATION OF A VOMEROPHERIN, AND VOMEROPHERIN-EMITTING ALARM DEVICES

BACKGROUND OF THE INVENTION

1. Field of the Invention

This invention relates to a method of increasing alertness in an individual by administering an effective amount of an alertness-increasing Vomeropherin to the individual; and to an alarm device that, when activated, emits an alertness-increasing vomeropherin. The method and device are especially useful in increasing alertness in individuals who are not readily responsive to external stimuli.

2. Background Information

Fire and smoke alarms are designed to alert the occupants of a building of the development of a fire. In recent years, they have been considered an essential life-saving device and have become a standard feature in most homes and commercial buildings. Most of the home fire alarms currently on the market produce an audible signal to warn and/or awaken individuals who are in the vicinity of a developing fire. Some fire alarms also produce visible signals such as flashing lights.

Carbon monoxide alarms are designed to alert the occupants of a building of carbon monoxide gas in the atmosphere of the building. They are becoming more popular for home use, since carbon monoxide cannot be detected by an unaided individual (the gas is colorless and odorless), and is the product of incomplete combustion and may be the product, for example, of either fire or, more commonly, a malfunctioning gas appliance such as a furnace. These alarms also typically produce an audible signal, and may also produce a visible signal.

Alarms may also be used to indicate the presence of other alarm conditions, which include but are not limited to, presence of radon (a tasteless, odorless, and invisible gas), propane gas, methane, apnea (suspension of respiration), or unauthorized entry (for burglar alarms).

Alarms may also be used to indicate the presence of an alarm condition (generally, in a non-hazardous situation) in which there is a request for an individual to respond, such as a ringing phone (request for the individual to answer the phone), a buzzing or ringing alarm clock (request for the individual to awaken), a ringing doorbell (request for the individual to answer the door), and the like.

However, for individuals who have a tendency to sleep deeply, whether normally, because of a sleeping disorder, because of drug- or alcohol-induced sleepiness, or because of conditions such as anosmia (lack of sense of smell), healing impairment, or blindness, the usual stimuli (either direct hazard-related stimuli such as the presence of smoke, or stimuli from alarm systems) may be ineffective in warning them of the alarm condition and enabling them to take appropriate action.

It is therefore desirable to develop a method of increasing the alertness of an individual. It is also desirable to develop an alarm device that would increase the alertness of an individual in the presence of an alarm condition, to enable the individual to respond more effectively to the alarm condition.

SUMMARY OF THE INVENTION

In a first aspect, this invention provides a method of increasing alertness in an individual, comprising administering to the vomeronasal organ (VNO) of that individual an alertness-increasing effective amount of a compound of the formula:

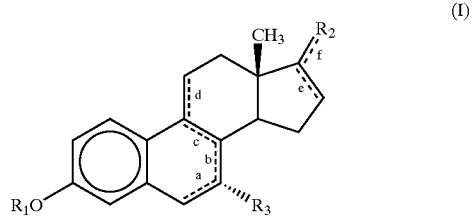

(I)

where:
$R_1$ is hydrogen, $C_{1-5}$ alkanoyl, or —$SO_3H$ or a salt thereof,
$R_2$ is hydrogen or methylene;
$R_3$ is hydrogen or $C_{1-4}$ alkyl;
one or two non-adjacent members of "a", "b", "c", and "d" are optional double bonds; and
when $R_2$ is hydrogen, "e" is either a double bond or a 16α, 17α-epoxide, and
when $R_2$ is methylene "e" is absent and "f" is a double bond.

In a second aspect, this invention provides an alarm device for alerting an individual to the presence of an alarm condition, comprising:
(a) a detector for the presence of the alarm condition, and
(b) a dispenser for administering to the vomeronasal organ of the individual an alertness-increasing effective amount of a compound of the formula:

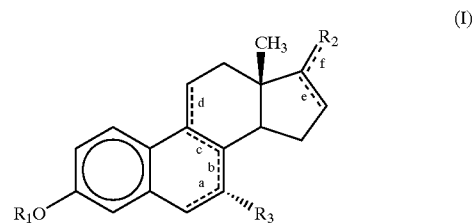

(I)

where:
$R_1$ is hydrogen, $C_{1-5}$ alkanoyl, or —$SO_3H$ or a salt thereof;
$R_2$ is hydrogen or methylene;
$R_3$ is hydrogen or $C_{1-4}$ alkyl;
one or two non-adjacent members of "a", "b", "c", and "d" are optional double bonds; and
when $R_2$ is hydrogen "e" is either a double bond or a 16α, 17α-epoxide, and
when $R_2$ is methylene, "e" is absent and "f" is a double bond; and, optionally,
(c) a warning means.

DETAILED DESCRIPTION OF THE INVENTION

Definitions

Unless otherwise stated; the following terms used in the specification and claims have the meaning given below.

"Alertness" includes wakefulness and responsiveness to external stimuli. Thus, "increasing alertness in an individual" includes either or both of awakening that individual and increasing that individual's responsiveness to an external stimulus, an effect that may take place with lightening of a state of sleep but without full awakening. Thus, increasing alertness in an individual would mean increasing the responsiveness of that individual to external stimuli, such as a bell ringing, phone ringing, fire, smoke, and the like.

An "alarm condition" with respect to an individual is one in which the safety or health of that individual or others may be adversely affected by the lack of a response by that individual, or one in which there is a request for an individual to respond. Exemplary alarm conditions in which the safety or health of that individual or others may be adversely affected by the lack of a response by that individual include fire, smoke, toxic gas (such as carbon monoxide), unauthorized entry (e.g. into the individual's residence), and the like. Exemplary alarm conditions in which the safety or health of others may be adversely affected by the lack of response include the conditions listed above and others such as, for example, apnea (such as of a sleeping infant—baby monitors are commercially available to warn parents of such an occurrence). It also includes conditions in which an ailing person (such as a person with pulmonary or cardiovascular disease) may require immediate assistance and may summon assistance with a "call buzzer" or the like, particularly in a home health setting where the responding individual may not remain awake all night. Exemplary alarm conditions in which there is request for an individual to respond (generally, in non-hazardous situations) include, a buzzing alarm clock (request for an individual to awaken), a ringing phone (request to answer the phone), a ringing door bell (request to answer the door), and the like. An "alarm" or "alarm device" for such alarm conditions therefore includes not only an alarm in which the alarm condition is detected by detection of the presence of a condition in which the safety or health of that individual or others may be adversely affected by the lack of a response by that individual, but also by the detection of a condition in which there is a request for the individual to respond.

"$C_{1-4}$ Alkyl" refers to a cyclic, branched or straight chain monovalent hydrocarbon radical of 1 to 4 carbon atoms, such as methyl, ethyl, propyl, 2-propyl, cyclopropyl, butyl, 2-butyl, 2-methylpropyl, 1,1-dimethylethyl, and cyclopropylmethyl.

"$C_{1-5}$ Alkanoyl" refers to the group —C(O)—R where R is hydrogen or $C_{1-4}$ alkyl.

An "effective amount" refers to an amount sufficient to increase the alertness of an individual.

A "vomeropherin" is a compound that functions as a chemosensory messenger, binds to a specific vomeronasal neuroepithelial receptor, and induces a physiological or behavioral effect. The effect of a "vomeropherin" is mediated through its interaction with the vomeronasal organ (VNO).

The transitional term "comprising" is an open-ended term synonymous with "including" and does not exclude additional unrecited elements.

The Vomeropherins

The alertness-increasing vomeropherins usable in this invention are compounds of the formula:

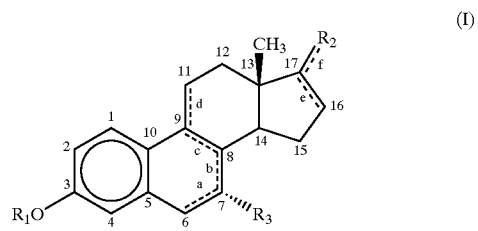

where:
$R_1$ is hydrogen, $C_{1-5}$ alkanoyl, or —$SO_3H$ or a salt thereof;
$R_2$ is hydrogen or methylene;
$R_3$ is hydrogen or $C_{1-4}$ alkyl;
one or two non-adjacent members of "a", "b", "c", and "d" are optional double bonds; and
when $R_2$ is hydrogen, "e" is either a double bond or a 16α,17α-epoxide, and
when $R_2$ is methylene, "e" is absent and "f" is a double bond.

The 13-position in these compounds is a chiral center, and the 13-methyl has the β configuration. When both "a" and "b" are absent and $R_3$ is $C_{1-4}$ alkyl, the 7-position is also a chiral center, and the 7-alkyl has the α configuration.

A preferred vomeropherin is a compound of the formula above where $R_1$ is acetyl, $R_2$ and $R_3$ are hydrogen, "a", "b", "c" and "d" are absent, and "e" is a double bond, namely estra-1,3,5(10),16-tetraen-3-yl acetate.

Another preferred vomeropherin is a compound of the formula wherein $R_1$ is hydrogen, $R_2$ is methylene, $R_3$ is absent, "a", "c" and "f" are present and "b" and "d" are absent, namely, 17-methylene-1,3,5(10),6,8-pentaen-3-ol.

The vomeropherins useful in this invention may be prepared following the general procedures for the synthesis of steroids which are well-known to those skilled in the art (see for example, Fieser, L. F. and M. Fieser, *Steroids*, Reinhold, New York, 1959). The specific reaction conditions may be determined by routine experimentation.

Estra-1,3,5(10),16-tetraen-3-ol, for example, may be prepared from estrone (estra-1,3,5(10)-trien-3-ol-17-one) by reacting estrone with an appropriate amount of p-toluenesulfonylhydrazide in a polar solvent such as dry methanol or ethanol under reflux to form the corresponding estrone p-toluenesulfonylhydrazone. The estrone p-toluenesulfonylhydrazone is then reacted with n-butyl lithium in an inert aprotic solvent such as dry tetrahydrofuran, ether, dimethoxyethane or the like to give estra-1,3,5(10),16-tetraen-3-ol.

Acyl derivatives of estra-1,3,5(10),16-tetraen-3-ol are prepared by conventional means, for example, by treatment with an appropriate anhydride in ether/pynidine at room temperature.

The compound of formula wherein $R_2$ is hydrogen and "e" is a 16α, 17α-epoxide may be prepared according to the method as demonstrated in Example 3 below.

The salts of the compounds where $R_1$ is —$SO_3H$ may include metallic salts such as sodium, potassium, lithium salts and the like. The synthetic procedure for the salts is, specifically demonstrated in Example 4 below. The salt derivatives have the advantage that they crystallize and solubilize readily.

Purification of the products is accomplished by means of chromatography and/or crystallization, as known to those skilled in the art.

These vomeropherins have a psychostimulant effect including a primary arousing effect, evidenced by decreased total sleep time and increased sleep onset latency. They also increase an individual's alertness to external stimuli, such as stimuli associated with the presence of alarm conditions, e.g., fire, smoke, audible or visible alarms.

They have an alertness-increasing effect in normal individuals; however, they are expected to be particularly useful in individuals who have a tendency to sleep deeply, whether normally, because of a sleeping disorder, because of drug- or alcohol-induced sleepiness, or because of conditions such as anosmia (lack of sense of smell), hearing impairment, or blindness, that makes them less responsive to stimuli, especially the usual stimuli associated with hazardous conditions.

Administration and Delivery

1) Vomeronasal Organ (VNO)

The present invention involves a non-systemic delivery of an alertness-increasing vomeropherin to the VNO. Delivery provides for contacting neurochemical receptors in the VNO, also known as "Jacobson's organ," with such vomeropherin. The VNO is a small bilateral nasal organ with a central lumen and a pit opening to the nasal cavity. The lumen is lined with sensory neuroepithelia which constitute a distinct locus of chemosensory receptors. The chemosensory cells of the VNO neuroepithelia form the vomeronasal nerve and have direct input to the cortico-medial amygdaloid basal forebrain and hypothalamic nuclei of the brain. The distal axons of terminalis nerve neurons may also serve as neurochemical receptors in the VNO.

2) Compositions and Methods of Delivery

The vomeropherins of this invention are administered to individuals through emission into the environment.

These vomeropherins may be emitted into the environment by an aerosol dispenser, (intended for spraying into large enclosed areas), using a propellant gas to deliver the vomeropherin as a fine spray or mist. A typical dispenser contains a suspension or solution of the vomeropherin admixed with a liquefied gas propellant, or with a combination of water, ethanol, and a propellant. The propellant may be one or more gases such as chlorofluorocarbons (CFCs) or other non-CFC gases that are non-toxic and non-flammable. The propellant must also be volatile so that when the propellant is released in the air it evaporates leaving only the alertness-increasing vomeropherin. An aerosol dispenser where non-liquefied pressurized gas propellants are in a separate chamber from the aerosol solution (containing the vomeropherin) can also be used. Examples of possible propellants include nitrogen, carbon dioxide, and nitrous oxide.

When delivered through the use of an aerosol, unless dissolved, the compound is present in finely and uniform divided form. Typical percentages of the compound present in the aerosol composition are 0.001 to 2% by weight, preferably 0.004 to 0.10%.

The aerosol composition may also contain a surfactant. Suitable surfactants must, of course, be nontoxic and preferably soluble in the propellant. Representative of such surfactants are the esters or partial esters of fatty acids containing from 6 to 22 carbon atoms, such as caproic, octanoic, lauric, palmitic, stearic, linoleic, eleostearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may also be employed. The preferred surfactants are sorbitan oleates, e.g., those sold under the trademarks "Arlacel C" (sorbitan sesquioleate), "Span 80" (sorbitan monoleate) and "Span 85" (sorbitan trioleate). The surfactant may constitute 0.1–20% by weight of the composition, preferably 0.25–5%.

In producing the aerosol, a container equipped with a suitable valve is filled with an appropriate propellant, the finely divided compound and optionally a surfactant. The ingredients are maintained at an elevated pressure until released.

When the vomeropherins are delivered as a vapor, the delivery means are well known to those skilled in the art of neurophysiology (for example, Tucker, D. and T. Shibuya, *Cold Spring Harbor Symp. Quant. Biol.* (1965) 30:207 and Vigouroux, M., et al, (*J. Neurosci. Methods* (1988) 24:57).

In a basic form, a vapor delivery means is a constant air flow source bubbled through a liquid medium. These vomeropherins may also be impregnated in a material (preferably with a weight ratio of 1/30) such as a sponge or cotton in a dry powdered or crystalline form for delivery as a vapor. The vapor may be regulated by a single parameter or in combination—for instance, purity, temperature, water vapor tension, flow rate, and the like. Various stimulants for instance an odorant, a flavoring, a drug, or the like, may be introduced into the vapor stream either continuously, or preferably, as a pulse of particular duration. The crystals when delivered must be of uniform size with no large clumps.

These vomeropherins may also be formulated into a liquid composition such as a solution which is sprayed into the environment. In this case, a variety of non-toxic and non-inflammable solvents or solvent mixtures which are capable of dissolving the vomeropherins are suitable, for example, ethanol, propylene glycol and DMSO (dimethyl sulfoxide). Usually an aqueous ethanol solvent is preferred. The preferred concentration of the ethanol in the mixture is in the range of 1 to 4% (v/v). However since the solution is not administered directly to the nasal passage, an aqueous ethanol solvent with a higher concentration of the ethanol would also be acceptable.

The concentrations of the vomeropherins in the compositions described above may vary. However they must be sufficiently high to deliver, when emitted into the environment, an effective amount of the compound to the individuals.

3) Effective Dose Level

The vomeropherins of this invention are effective in increasing alertness in both male and female, although there may be gender variations in the dose levels at which the compounds are effective, the dose range is 0.1 ng/100 $\mu$l to 100 $\mu$g/100-$\mu$l. A single administration of at least about 200 picograms, delivered directly into the lumen of the VNO, is effective in eliciting a transient autonomic response. When administered to the nasal cavity, the amount is about 100 picograms to about 100 micrograms, preferably about 1 nanogram to about 10 micrograms, more preferably about 10 nanograms to about 1 nicrogram.

The doses will be as above if the dose is to be administered by a device directly to the individual's VNO or nose. If the dose, however, is to be administered providing a sufficient concentration of the vomeropherin in the air surrounding the individual(s), so that it contacts the individual(s)'s VNO by inhalation through the nose or diffusion into the nasal cavity, then the quantity of the vomeropherin to be dispersed to achieve that dose will be substantially higher depending on factors such as the individual being alerted, the number of individuals in the room, the size of the room, and the placement of the dispenser.

For example, considering that humans at rest on average displace 4 liters of air per minute, a dispenser containing 100 mg of vomeropherin is sufficient to saturate a volume of 25 cubic meters, the approximate volume of a 9ft.×12 ft×8 ft room; and a dispenser containing 8 mg of vomeropherin is sufficient to saturate a volume of 2 cubic meters, such as when the dispenser is mounted on the headboard of a bed. Even if the room has continuous air flow, the loss of vomeropherin in the air will be negligible.

Thus, a person of ordinary skill in the art, with the skill and this disclosure, can calculate the appropriate total quantity required to achieve an alertness-increasing effective amount in individuals.

Alarm Devices

A typical alarm device (whether for hazardous and non-hazardous situations) consists of a detector to sense the presence of an alarm condition (such as, but not limited to, presence of fire, smoke, unauthorized entry, or request to answer the phone), and one or more warning means, such as a horn or a flashing light, to generate an alarm signal. A detector in a smoke alarm, for example, senses the presence of smoke, through photoelectric or ionization means. Once the detector senses the presence of smoke, an electric signal is sent to the sounder auxiliary relay activating the warning means, such as a horn, thus generating an alarm signal.

There are typically two types of smoke alarms. Ionization smoke alarms use an ionization chamber, which consists of two plates with a voltage across them, along with a radioactive source of ionizing radiation, generally a very small amount of americium-241. The detector operates by measuring the change in ionization caused by smoke entering the chamber.

Photoelectric smoke alarms, on the other hand, use light and a light detector to sense a developing fire. In a normal condition, the light from the light source shoots straight across and misses the detector. Smoke particles, however, scatter the light and, consequently, some amount of light hits the detector activating the warning means, such as a horn.

A detector in a carbon monoxide (CO) alarm measures levels of CO over time. It may be a higher amount of CO over a short period of time or a lower amount for an extended time frame. In either case, when the detector senses a certain saturation level of CO, an electric signal is sent triggering the horn.

Using the detectors of alarm devices, such as, but not limited to, detectors for smoke, carbon monoxide, unauthorized entry, call connection, or pressed door bell, an alarm device of the present invention can be made comprising of a detector sensing the alarm condition and a dispenser containing the alertness-increasing vomeropherin. Waning means producing an audible and/or visible signal, such as a horn or a light, may also be incorporated into the alarm device.

The dispenser may, be contained within or outside the alarm device. The dispenser, in practice, is preferably placed in allocation which is near the individual, for example near the bed of the individual to allow the vomeropherin to be received by the individual more readily.

In any case, once the detector senses the alarm condition, the dispenser is activated to release the alertness-increasing vomeropherin, thereby increasing the alertness of individuals. The other warning means, if present, are also activated.

The invention is illustrated by the following examples.

EXAMPLE 1

Synthesis of Estra-1,3,5(10),16-tetraen-3-ol
Estrone p-Toluenesulfonylihydrazone Estrone (270 g, 1.00 mol) and p-toluenesulfonylhydrazide (232.8 g, 1.25 mol) in dry methanol (2.5 liters) were heated under reflux for 20 hours. The mixture was transferred to a conical flask and allowed to cool. The crystalline product was filtered off under suction and washed with methanol (300 ml). Further crops of product were obtained by sequentially evaporating the filtrate to 2000 ml, 800 ml and 400 ml, and allowing to crystallize each time. Total yield was 433.5 g (99%).

1,3,5 (10),16-Estratetraen-3-ol

Estrone p-toluenesulfonylhydrazone (219.0 g, 500 mmol) in dry tetrahydrofuran (8.0 liters) was cooled in a sodium chloride/ice bath. The mixture was mechanically stirred while n-butyl lithium (800 ml of a 2.5 M solution in hexane, 2.00 mol) was added via double-ended needle. The mixture was stirred at room temperature for 3 days. Ice (250 g) was added, followed by saturated ammonium chloride solution" (500 ml). The phases were mixed by stirring and then allowed to settle. The aqueous phase was removed via aspiration with teflon tube and extracted with ether (500 ml). The two organic phases were sequentially washed with the same bath of saturated sodium bicarbonate solution (500 ml) followed by saturated sodium chloride solution (500 ml). The organic layers were dried ($MgSO_4$) and evaporated in vacuo to give crude product. This was subjected to flash filtration on 500 g silica gel 60, 230–400 mesh, eluting with ethyl acetate/hexane (25:75, 2.5 liters). The filtrate was evaporated in vacuo to give crystalline material. The product was recrystallized from methanol (300 ml)/water (75 ml) washing with methanol (80 ml)/water (20 ml). Further recrystallization from ethyl acetate/hexane (12.5:87.5) gave pure product (88.9 g, 70%).

EXAMPLE 2

Synthesis of Estra-1,3,5(10),16-tetraen-3-ol-acetate

To 1,3,5(10),16-estiatetraen-3-ol (254 mg, 1.00 mmol) in ether (10 ml) is added acetic anhydride (0.25 ml) followed by pyridine (0.25 ml) and the mixture is stirred at room temperature for 16 hours. The mixture is poured into ice/water and extracted with ether (2×20 ml). The organic extracts are washed with water, saturated copper sulfate solution, water, and saturated sodium chloride solution, dried ($MgSO_4$) and evaporated in vacuo to give the crude material. This is purified by flash chromatography on 17.5 g silica gel 60 (230–400 mesh) eluting with 10%–12% ethyl acetate/hexane to give the pure product (192 mg, 65%). Other esters may be prepared using the appropriate anhydride.

EXAMPLE 3

Synthesis of Epoxide of Estra-1,3,5(10),16-tetraen-3-ol-acetate

3-Chloroperoxybenzoic acid (862.9 mg, 5.000 mmol) in 25 ml of 1,2-dimethoxyethane (DME) was added to a solution of estra-1,3,5(10),16-tetraen-3-ol (636.0 mg, 2.500 mmol) in 15 ml of DME. After stirring for 6 hours, the reaction mixture was poured into 140 g of 5% (w/w) sodium thiosulfate pentahydrate and extracted into three 100 ml portions of ethyl acetate. The combined extracts were washed with 100 ml of saturated sodium bicarbonate and three 100 ml portions of brine, dried over magnesium sulfate, and filtered through Celite 503. The residue was washed with 50 ml of ethyl acetate and the combined filtrates were concentrated under reduced pressure. Flash chromatography (20% ethyl acetate/hexane on silica gel) of the residue, followed by crystallization from ethyl acetate, produced lustrous, white platelets (349.9 mg, 1.294 mmole, 52%), m.p., 217–219° C., homogeneous to TLC (20% ethyl acetate/hexanes on silica gel; $R_f$0.32; starting material $R_f$0.50).

Acetic anhydride (0.70 ml, 7.4 mmol) was added to a suspension of the material prepared from the procedure above(400.0 mg, 1.479 mmol) in anhydrous pyridine (2.4 ml, 30 mmol). After stirring for 18 hours, methyl t-butyl ether (MTBE, 15 ml) was added and the reaction mixture was washed with three 5 ml portions of 1N HCl, 5 ml of saturated copper sulfate, 5 ml of saturated sodium bicarbonate; and 5 ml of brine, dried over magnesium sulfate, and filtered through Celite 503. The residue was washed with 5 ml of MTBE and the combined filtrates were concentrated under reduced pressure. Recrystallization of the residue from 95% ethyl acetate with intermediate treatment with charcoal yielded fine, white platelets (295.1 mg, 0.9446 mmole, 64%), m.p., 114–115° C., homogeneous to TLC (20% ethyl acetate/hexanes on silica gel; $R_f$0.36; starting material $R_f$0.24).

EXAMPLE 4

Synthesis of Estra-1,3,5(10),16-tetraen-3-yl Sulfate Potassium Salt

Sulfur trioxide/pyridine complex (3.8 g, 23.9 mmol) was added to estra-1,3,5(10),16-tetraen-3-ol (1.00 g, 5.93 mmol) in 10 ml dry dimethylformaimide (stored over molecular sieves). After stirring for 4 hours, the suspension was added dropwise, with rapid stirring, to triethanolamine (11.73 g, 78.62 mmol) in 200 ml of water, and the resulting solution was filtered through a coarse glass frit. The filtrate was added to potassium carbonate (7.00 g, 50.6 mmol) in 20 ml of water with rapid stirring and then filtered through a coarse glass frit. The residue was washed with 10 ml water, and then dried over $P_2O_5$ under vacuum to give a solid (1.37 g, 3.68 mmol, 94% yield), m.p. 210–215° C. (dec.).

EXAMPLE 5

Three methods were used to assess sleep: 1) sleep study, 2) quantitative electroencephalography, and 3) psychometric tests. The study was carried out using a randomized, single-blind, placebo-controlled experimental design.

1. Selection and Preparation of the Participants

Screening was performed several days prior to the study session via clinical interviews and examination. Additionally, Hamilton A and D, and Covy tests were administered to determine concomitant anxiety or affective disorders. A thorough questionnaire regarding sleep habits and sleep pathologies was also administered to each subject. Criteria for inclusion in the study included subjects with a score of 12 or less on the Covy test and a score of 8 or less on the Hamilton A and Hamilton D tests, and absence of any medical or psychiatric conditions. Ten physically and mentally healthy young male adult subjects were selected for the study. All of them Were normal sleepers (i.e., they reported no difficulty in falling or remaining asleep at night, slept between 6 and 8.5 hours per night, and were alert during the daytime).

On the day of the study, they were instructed to refrain from napping, to avoid consuming alcohol or caffeine containing beverages, and to maintain a uniform daily level of activity. The ten subjects were divided into two groups of five, with the test compound being administered to one group and the other acting as a control.

2. Preparation of Test Compound

The test compound was administered to the VNO using a manual vomeronasal applicator (MVA). This applicator comprises an air supply, delivering a 1 ml pulse of air; a valve system passing that pulse of air either through a chamber containing 30 mg of USP cotton that has been previously soaked with 1 ml of a 1 mg/ml solution of the test compound, estra-1,3,5(10),16-tetraen-3-yl acetate, in ethanol and allowed to dry overnight, or bypassing that chamber; a one-way flow valve; and a nozzle capable of being positioned in a nostril to provide direct administration to the lumen of the VNO. With a 1 ml air pulse, the MVA delivers 200 pg of the test compound to the VNO.

3. Polysomnography and VNO Stimulation

During the study, subjects spent one night in the sleep laboratory and underwent conventional polysomnography (PSG) only, during the first hour. The criteria for this short recording was based on previous findings showing that single dose VNO stimulation with the vomeropherins induced effects within one hour after stimulation. Before starting the recordings, each subject was questioned regarding distressing or extenuating events during that day that could contribute to sleep disruption. Times of last meal and physical exercise (if applicable) were also recorded. In order to determine whether the compound would affect daytime activities, or anterograde memory, judgment and motor skills were also evaluated both before going to sleep and in the morning. For this purpose, subjects were administered a maze test, a digit-symbol substitution test, a right and left manual coordination test (dot test), and a number repetition test as described in a previous publication (Monti, J. M., 1989, Slow Wave Sleep in Health and Disease. In: Waukier A., Dugovic C. and Radulovacki M. "Slow Wave Sleep." New York, Raven Press. pp. 331–322).

Immediately prior to "lights out", subjects were asked to lie in a supine position. The MVA was positioned in the right nostril, with its nozzle directed toward the right VNO opening. Later, the MVA was positioned in the left nostril for stimulation of the left VNO. Two pulses of air or the test compound or placebo were administered to each VNO. The same procedure was repeated 30 minutes later, at which times the investigator would enter the room and wake the subject if he was asleep, so that the total dose of the vomeropherin being administered to each subject was 800 pg.

At each 30 minute sleep interruption, prior to the test compound application, each subject was given a short questionnaire to record his perception of whether he was asleep, estimated time spent awake, and number of awakenings. In addition, sleepiness was measured by a 3 item analog scale inventory (scored from 0 to 10, higher numbers indicating more sleepiness) that included: a) readiness to get back to sleep; b) degree of anxiety and c) self rated level of sleepiness. The scale displayed opposite states on the ends of a horizontal line, including "completely awake-completely asleep", "extremely restless-extremely calm" and "I want to sleep but feel I cannot—I can get back to sleep very easily". Recordings began at 10:00 p.m. and lasted until 6:00 a.m. of the following day. Frontal, parietal and occipital electroencephalograms (EEG), electrooculograms, and electromyograms were recorded during the first hour. These recordings were coded and scored blind for non-rapid eye movement sleep latency from "lights out" to the appearance of the first minute of Stage 1 sleep, total wake time, wake time after sleep onset, and total sleep time. Sleep stages were assigned according to the criteria of Rechtschaffen and Kales (1968). All variables were scored separately for each 30-minute interval. Number of awakenings was tallied for the entire hour of recording.

In the morning, all subjects completed a multiple-choice questionnaire regarding the following variables: sleep latency after last entry, estimated time sleeping, number of awakenings, and quality of sleep. General status at waking time was determined by marking on a 9 item analog scale inventory. In addition, all subjects were administered cognitive and motor performance tests identical to those received before bedtime.

4. Scoring of Sleep Parameters

Sleep variables evaluated in this study included Total Sleep Time (TST) or amount of sleep during the recording period, Sleep Efficiency (SE) or percentage of sleep, Sleep Onset Latency (SOL) or time to fall asleep after recordings begun. Sleep was consolidated when the first complete minute of Stage 1 sleep was attained. Non-REM sleep was scored by the appearance of Stages 1, 2, 3 and 4 and REM sleep by the appearance of a desynchronized brainwave pattern, eye movements and flat muscle tone. Latency to each of these stages was also determined, with particular scrutiny of REM sleep latency. Duration of each stage was also determined and expressed in percentage of total sleep time (dividing the duration of each sleep stage by the total sleep duration, and multiplying by 100). Each subject also reported his sleep experience by answering a brief questionnaire and a visual analog scale.

5. Test Results

A. Assessment through Polysomnography

The PSG results are summarized in Table 1 and show that the test group had a longer SOL, a shorter TST, and a shorter wake time after sleep onset as compared to the control group.

The SOL for the control group was 16 minutes as compared to 21 minutes of the test group. The TST for the control group was 26 minutes as compared to 14.3 minutes of the test group. A statistical significance of $P<0.05$ is obtained for the SOL and TST.

B. Subjective Assessment a) Subjective Assessment—Self-Evaluation at Half-hour Intervals The control group reported a sleep latency longer than 10 minutes, with a varied number of awakenings among subjects, ranging from none to more than three. In the test group, sleep latency was reported in the range between 10 and 30 minutes with three or more awakenings.

b) Subjective Assessment—Self-perception of Sleepiness

The results are summarized in Table II and indicate scores on the sleepiness scale inventory. At the beginning of the study, the test group did not show significant variations from the control group. After dosing, the control groups reported less sleepiness.

c) Sleep Latency

As shown in Table III, the control group had sleep latencies shorter than 30 minutes, whereas the test group reported latencies longer than 30 minutes.

d) Sleep Duration

As shown in Table IV, the test group reported total sleep duration between 4 and 6 hours while the control group reported sleeping for 7 to 8 hours.

e) Sleep Quality

Quality of sleep was classified by subjects as either "disturbed" or "undisturbed". Most subjects responded that their sleep was "undisturbed". However, one subject in the test group defined his sleep as "disturbed".

f) Condition at Morning Waking

Responses to the subject's state at the time of wake were indexed as "calm and refreshed", "tired" or "sleepy". In their answers, all marked being "calm and refreshed" or "tired" independently of treatment modality. Morning status assessed by a visual analog scale did not show any difference among groups treated with placebo or the test compound.

g) Motor Skills Cognitive Test

Neither the control nor the test group revealed any changes in scores between their night and morning tests for anterograde memory, judgment or motor dexterity.

6. Conclusions

The test compound, estra-1,3,5(10),16-tetraen-3-yl acetate has shown a primary arousing effect, evidenced by decrease in TST. In subjects treated with the test compound, a correlation in sleep latency between recordings and self reported answers were evident. One subject reported sleeping poorly, which corresponded to short total sleep time in the PSG.

The control group reported similar results in both subjective evaluation and PSG findings. In-session self-reports of sleepiness by the analog scale were coherent with PSG data. The above data seem to indicate that the test compound does not impair a subject's self-perception of sleep. The assertion is further supported by the lack of changes in cognition tests before and after treatment.

On the morning quiz, the test group reported sleep latencies longer than 30 minutes after VNO stimulation as opposed to the control group which indicated falling asleep in less than 30 minutes. The test group also reported spending less time sleeping, as compared to the control group. Combined with PSG data from the test group, the above significant finding seems to indicate a possible psychostimulant effect of the test compound.

TABLE I

Effect In Human Subjects Treated with Estra-1,3,5(10),16-Tetraen-3-yl Acetate and Placebo Assessed through a Polysomnography

| | Control Group Mean (minutes) | Test Group Mean (minutes) |
|---|---|---|
| Sleep Onset Latency (SOL) | 16 | 21 |
| Wake Time after Sleep Onset | 17.7 | 16.3 |
| Total Sleep Time (TST) | 26.0 | 14.3 |

TABLE II

Self-Perception of Sleepiness In Human Subjects Treated with Estra-1,3,5(10),16-Tetraen-3-yl Acetate and Placebo

| | First entry (beginning study) | Second entry (60 min. int) |
|---|---|---|
| Placebo | 7.5 | 8.9 |
| Test Compound | 6.0 | 3.2 |

TABLE III

Sleep Latencies

|  | <30 Minutes n | >30 minutes n |
|---|---|---|
| Test Compound | 0 | 5 |
| Placebo | 5 | 0 |

TABLE IV

Sleep Duration

|  | 4–6 hours | 7–8 hours |
|---|---|---|
| Test Compound | 5 | 0 |
| Placebo | 0 | 5 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular composition or device to a specific objective of the present invention. All such modifications are intended to be within the scope of the claims appended hereto.

What is claimed is:

1. A method of increasing alertness in an individual, comprising administering to the vomeronasal organ of that individual an alertness-increasing effective amount of a compound of the formula:

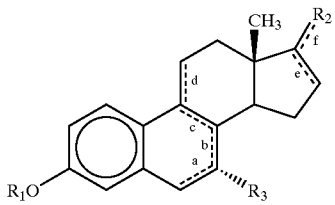

where:

R$_1$ is hydrogen, C$_{1-4}$ alkanoyl, or —SO$_3$H or a salt thereof;

R$_2$ is hydrogen or methylene;

R$_3$ is absent, hydrogen, or C$_{1-4}$ alkyl;

one or two non-adjacent members of "a", "b", "c", and "d" are optional double bonds; and when R$_2$ is hydrogen, "e" is either a double bond or a 16α, 17α epoxide, and when R$_2$ is methylene, "e" is absent and "f" is a double bond.

2. The method of claim 1 where the administration comprises emission of the compound into the environment around the individual.

3. The method of claim 1 where R$_1$ is acetyl, R$_2$ and R$_3$ are hydrogen, "a" "b", "c" and "d" are absent, and "e" is a double bond, namely where the compound is estra-1,3,5(10),16-tetraen-3-yl acetate.

4. The method of claim 1 for increasing the responsiveness to an external stimulus.

5. The method of claim 4 where the stimulus is an alarm signal.

6. An alarm device for alerting an individual to the presence of an alarm condition, comprising:

(a) a detector for the presence of the alarm condition, and (b) a dispenser, activated by the detector detecting the presence of the alarm condition, for administering to the vomeronasal organ of that individual an alertness-increasing effective amount of a compound of the formula:

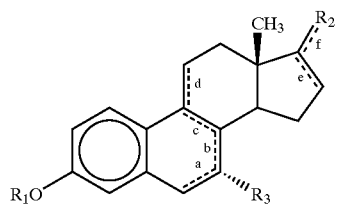

where:

R$_1$ is hydrogen, C$_{1-4}$ alkanoyl, or —SO$_3$H or a salt thereof;

R$_2$ is hydrogen or methylene;

R$_3$ is absent, hydrogen, or C$_{1-4}$ alkyl;

one or two non-adjacent members of "a", "b", "c", and "d" are optional double bonds; and when R$_2$ is hydrogen, "e" is either a double bond or a 16α, 17α epoxide, and when R$_2$ is methylene, "e" is absent and "f" is a double bond.

7. The alarm device of claim 6 where the dispenser emits the compound into the environment around the individual.

8. The alarm device of claim 6 where R$_1$ is acetyl, R$_2$ and R$_3$ are hydrogen, "a", "b", "c" and "d" are absent, and "e" is a double bond, namely where the compound is estra-1,3,5(10),16-tetraen-3-yl acetate.

9. The alarm device of claim 6 where the alarm condition to be detected is a fire.

10. The alarm device of claim 6 where the alarm condition to be detected is the presence of carbon monoxide.

11. The alarm device of claim 6 where the alarm condition to be detected is the presence of methane.

12. The alarm device of claim 6 where the alarm condition to be detected is the presence of propane.

13. The alarm device of claim 6 where the alarm condition to be detected is the presence of radon.

14. The alarm device of claim 6 where the alarm condition to be detected is the presence of apnea.

15. The alarm device of claim 6 where the alarm condition to be detected is the presence of unauthorized entry.

16. The alarm device of claim 6 that further comprises a warning means producing an audible and/or visible signal.

* * * * *